United States Patent [19]

Lundquist et al.

[11] Patent Number: 4,865,581
[45] Date of Patent: Sep. 12, 1989

[54] RETROPERFUSION CONTROL APPARATUS, SYSTEM AND METHOD

[75] Inventors: Ingemar H. Lundquist, Pebble Beach; Zoltan Tarczy-Hornoch, Berkeley; Thomas J. Kardos, Laguna Beach, all of Calif.

[73] Assignee: Retroperfusion Systems, Inc., Costa Mesa, Calif.

[21] Appl. No.: 56,401

[22] Filed: May 29, 1987

[51] Int. Cl.⁴ .............................................. A61M 1/00
[52] U.S. Cl. .................................. 600/18; 600/17; 604/67
[58] Field of Search .................. 128/1 D; 604/67; 600/16, 17, 18

[56] References Cited

U.S. PATENT DOCUMENTS

| | | | |
|---|---|---|---|
| 3,421,497 | 1/1969 | Chesnut et al. | 128/1 D |
| 4,014,318 | 3/1977 | Dockum et al. | 128/1 D |
| 4,137,913 | 2/1979 | Georgi | 604/67 |
| 4,175,264 | 11/1979 | Schiff | 128/1 D |
| 4,459,977 | 7/1984 | Pizon et al. | 128/1 D |
| 4,551,331 | 11/1985 | Zegers de Beyl et al. | 604/67 |
| 4,557,725 | 12/1985 | Heyne et al. | 604/67 |
| 4,598,697 | 7/1986 | Numazowa et al. | 128/1 D |
| 4,604,034 | 8/1986 | Wheeldon et al. | 604/67 |
| 4,718,576 | 1/1988 | Tamura et al. | 604/67 |

*Primary Examiner*—Lee S. Cohen
*Assistant Examiner*—K. Schaetzle
*Attorney, Agent, or Firm*—Flehr, Hohbach, Test, Albritton & Herbert

[57] ABSTRACT

Retroperfusion control apparatus for supplying arterial blood of a patient to the venous side of the patient's heart including a pump having an inlet and an outlet and a piston movable through a pump stroke for moving a liquid from the inlet to the outlet of the pump. A stepper motor is provided which drives the piston. Electronic circuitry is provided for driving the stepper motor and senses the presence of an R wave in a patient to operate the stepper motor in response to the sensed R wave.

29 Claims, 6 Drawing Sheets

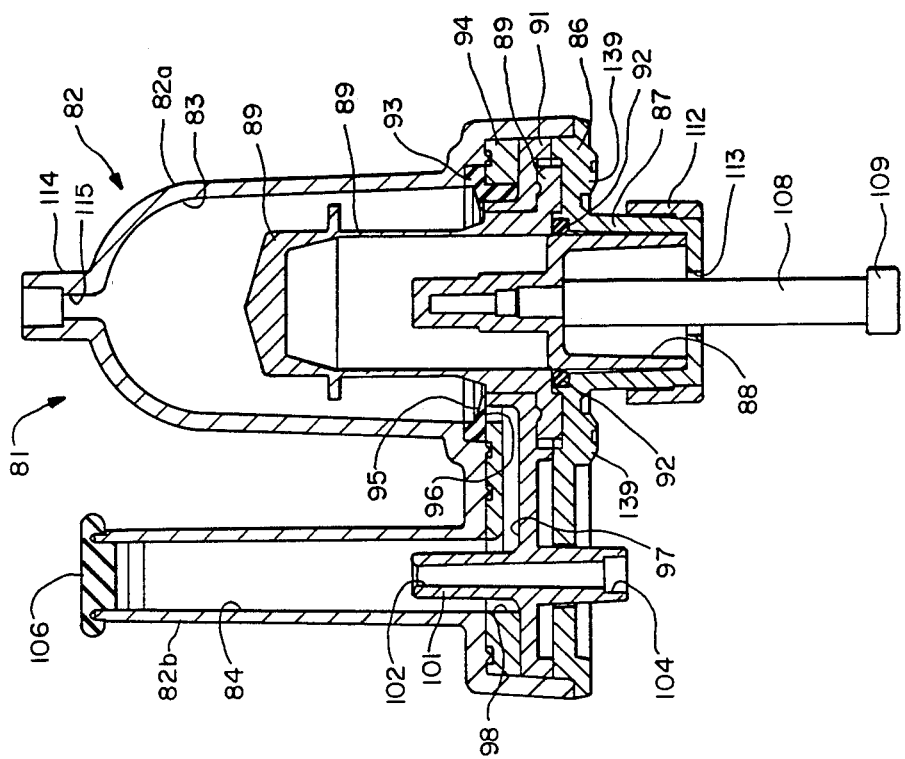
FIG.—5
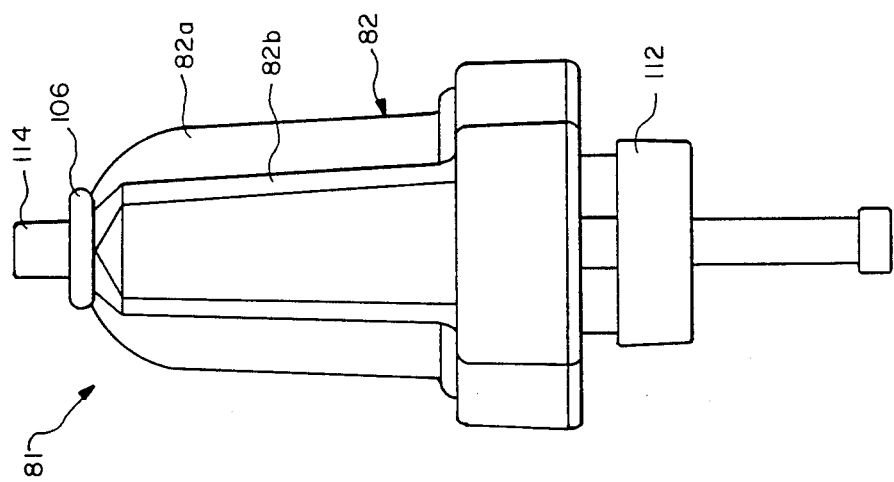
FIG.—4

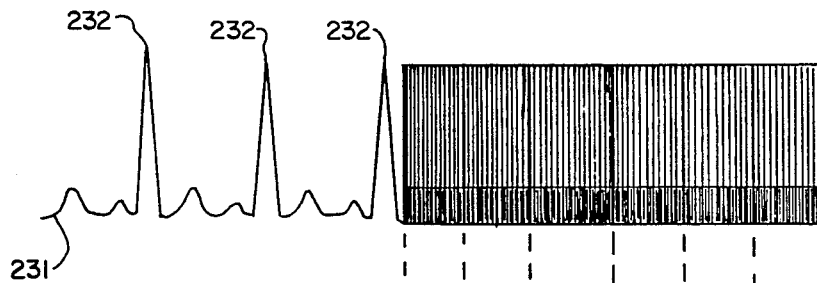
FIG.—7A
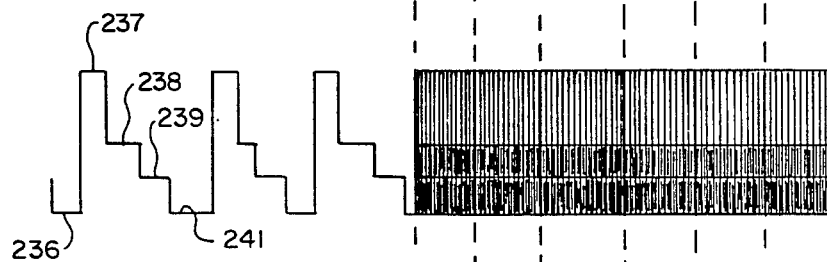
FIG.—7B
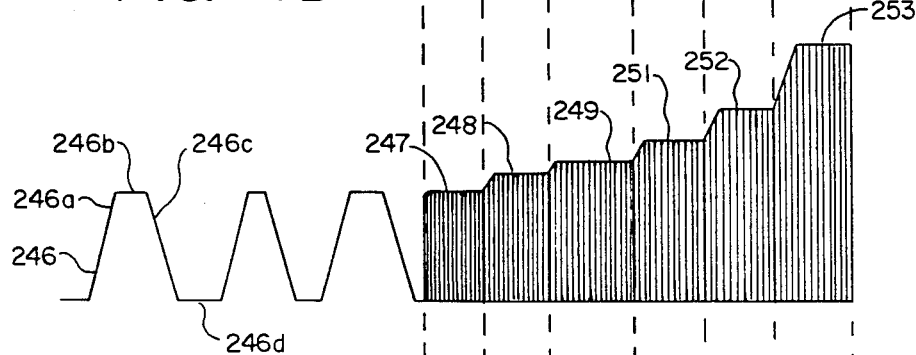
FIG.—7C
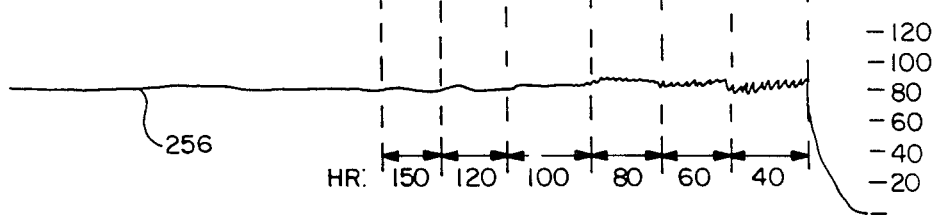
FIG.—7D  (FLOW SET = 80)

RETROPERFUSION CONTROL APPARATUS, SYSTEM AND METHOD

This invention relates to a retroperfusion control apparatus, system and method.

Attempts have heretofore been made to perform synchronized diastolic coronary venous retroperfusion. Results are published in the August 1985 issue of the *Journal of the American College of Cardiology*, Vol. 6, No. 2, pages 328-335 and in *Circulation*, August 1986, Vol. 74, No. 2, pages 381-388. Both of these articles describe work which was done in connection with a synchronous retroperfusion system (USCI Model ECI). Such a system consists of a Hewlett Packard 78346A monitor for display of cardiac rhythm, arterial pressure and the pump signal. The monitor is a two-channel unit which is capable of monitoring and displaying the electrocardiogram and pressure or pump timing. Information from the monitor is fed and processed by the pump controller which operates a piston driven pump to maintain pump flow and pump timing through feedback circuits that compensate for variations in the patient's heart rhythm and rate. The piston driven pump is of the disposable type and is connected through tubing between the arterial blood supply and an auto-inflatable retroperfusion balloon catheter which is positioned in the great cardiac vein via the coronary sinus. As arterial blood is delivered through the coronary sinus catheter during diastole, this arterial blood inflates a balloon at the tip of the catheter. Inflation of the balloon seals the coronary sinus preventing leakage of arterial blood and permits a more effective retrograde delivery of arterial blood into the myocardium. On termination of retrograde catheter perfusion at or near end-diastole, the reverse stroke of the pump creates a back flow into and through the catheter which attempts to deflate the balloon. The amount of balloon deflation is heart rate and flow rate dependent. This allows retrograde coronary sinus drainage of venous blood from the myocardium into the right atrium during systole. Even though such work has been carried out in connection with retroperfusion, there is a need for a new and improved apparatus and system for carrying out such retroperfusion and an improved method for accomplishing the same.

In general, it is an object of the present invention to provide a retroperfusion and retroinfusion control apparatus, system and method which makes it possible to accomplish retroperfusion and retroinfusion in humans more proficiently.

Another object of the invention is to provide a retroperfusion and retroinfusion apparatus, system and method of the above character in which adjustable delivery rate by stroke length and timing of pumping is utilized which is synchronized to the heart's R-wave signals.

Another object of the invention is to provide a retroperfusion control apparatus, system and method of the above character in which the pump cycle is always terminated at or before the beginning of a new R-wave.

Another object of the invention is to provide a retroperfusion control apparatus, system and method which utilizes a microcomputer for monitoring the R-waves for initiating and terminating the pump cycle.

Another object of the invention is to provide a retroperfusion control apparatus, system and method of the above character which can accommodate irregular heartbeats in the patient.

Another object of the invention is to provide a retroperfusion control apparatus, system and method of the above character in which a computer controlled stepping motor is utilized for providing an adjustable delivery rate such as by adjustable pump stroke and adjustable stepping rate.

Another object of the invention is to provide a retroperfusion control apparatus, system and method in which it is possible to specify delivery volume/time and/or delivery pressures.

Another object of the invention is to provide a retroperfusion control apparatus, system and method of the above character in which the pumping can be controlled with great precision.

Another object of the invention is to provide a retroperfusion control apparatus, system and method which utilizes a powered downstroke as well as powered upstroke.

Another object of the invention is to provide a retroperfusion control apparatus, system and method in which an active precisely controlled vacuum stroke of the pump motion is provided to accentuate deflation of the blood inflated balloon.

Another object of the invention is to provide a retroperfusion control apparatus, system and method in which the ECG signal from the patient is differentiated to find the maximum positive slope of the ECG waveform to provide an independent signal that an R wave is occurring or arterial pressure is differentiated to find a maximum negative slope to provide an independent signal that diastole is beginning.

Another object of the invention is to provide a retroperfusion control apparatus, system and method in which it is possible to more precisely ascertain when the R wave is occurring.

Another object of the invention is to provide a retroperfusion control apparatus, system and method in which a reversing action is utilized in the pump to facilitate deflation of the blood inflated balloon.

Another object of the invention is to provide a retroperfusion control apparatus, system and method which utilizes a pinch-off valve for shutting off blood flow during non-pumping modes.

Another object of the invention is to provide a retroperfusion control apparatus, system and method of the above character which utilizes a blood level sensor to detect blood supply problems such as an air leak or an occluded supply catheter or tubing.

Another object of the invention is to provide a retroperfusion control apparatus, system and method of the above character which incorporates numerous safety features.

Another object of the invention is to provide a retroperfusion control apparatus, system and method of the above character in which it is possible to deliver greater quantity of oxygenated blood to the area at risk even though the patient may have complex arrhythmias.

Another object of the invention is to provide a retroperfusion control apparatus, system and method of the above character in which the timing can be varied independently of blood flow to allow optimal perfusion of the myocardium.

Additional objects and features of the invention will appear from the following description in which the preferred embodiment is set forth in detail in conjunction with the accompanying drawings.

FIG. 4 is a front elevational view of a disposable pump incorporating the present invention.

FIG. 5 is a side elevational view in cross section of the pump shown in FIG. 4.

FIGS. 7A, 7B, 7C and 7D are strip chart recordings showing test results of the apparatus of the present invention at different heart beat rates.

Figure 1:
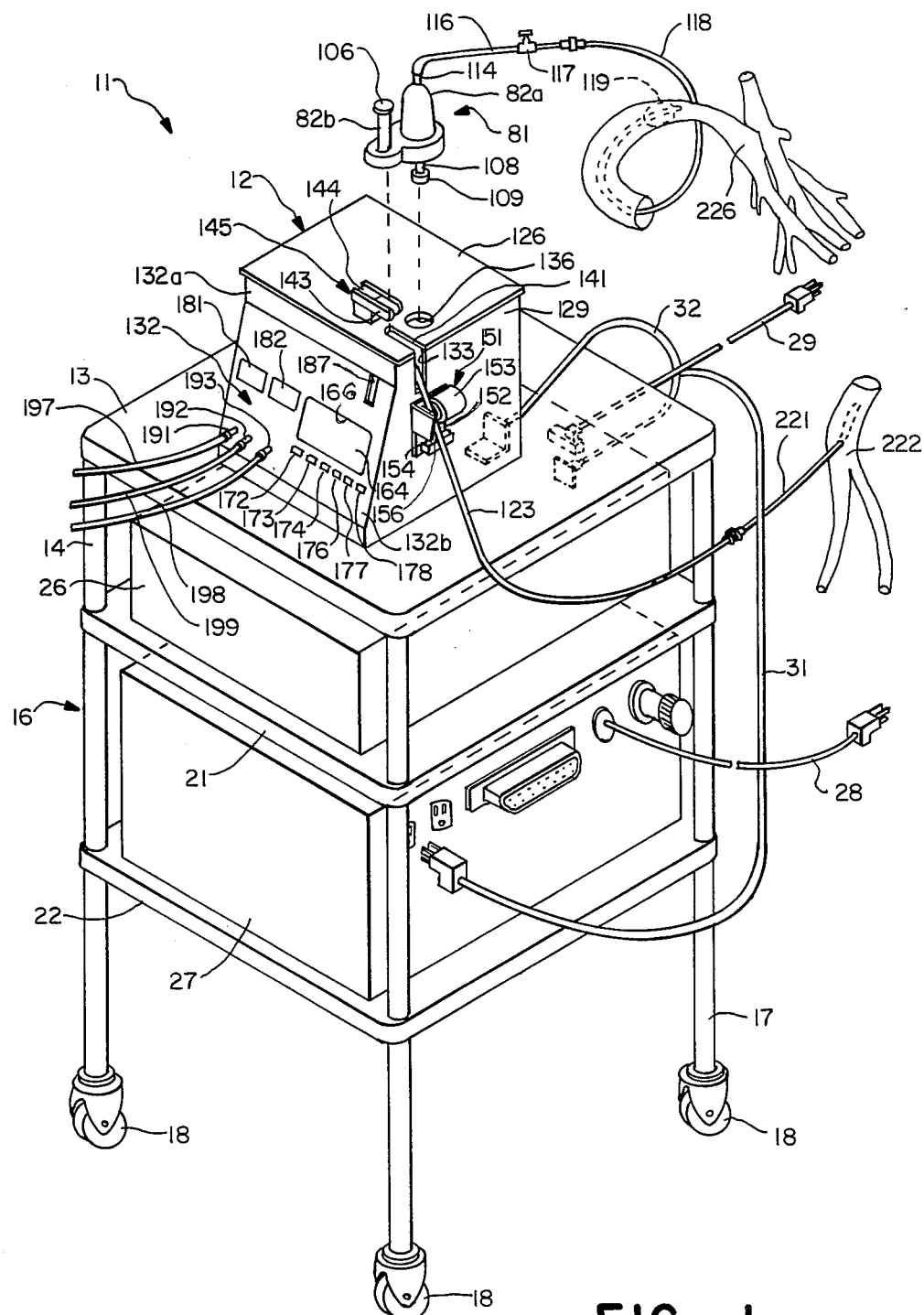
FIG. 1 is an isometric view of a retroperfusion control apparatus and system incorporating the present invention and showing the disposable pump about to be inserted into the same.

In general, the retroperfusion and retroinfusion control apparatus is comprised of a positive displacement pump having an inlet and an outlet, piston-like means for moving liquid from the inlet to the outlet, a stepper motor, means coupling the stepper motor to the piston-like means for causing operation of the piston-like means, electronic circuitry for driving the stepper motor, the electronic circuitry including means for sensing the R wave of a patient for operating the stepper motor, and for displaying the electrocardiagram, R wave, and pump stroke timing in relation to the above.

More in particular, the retroperfusion control apparatus and system 11 consists of a pump console 12 which is supported on the top level 13 of an equipment dolly or stand 14. The equipment dolly or stand 14 is provided with a rectangular framework 16 which has four depending legs 17 having casters 18 mounted on the bottom extremities of the same. The equipment dolly or stand 14 is provided with an intermediate level shelf 21 and a lower level shelf 22 which are carried by the legs 17.

A power supply 26 for the pump console 12 is mounted upon the intermediate shelf 21. A backup power supply 27 of the battery type is mounted on the lower shelf 22. The backup power supply 27 is provided with a conventional electrical cord 28 which is adapted to be connected to a conventional source of ac, as for example, 110 volts 60 cycle ac. The power supply 26 is provided with a similar electrical cord 29 which also is adapted to be connected to either a conventional type ac outlet or the backup power supply 27. Another electrical cord or cable 31 is provided which interconnects the backup power supply 27 to the power supply 26. A cord 32 connects the power supply 26 to the pump console 12.

The pump console 12 is provided with an internal metal framework 36 which is divided into a pump drive compartment 37 a monitoring compartment 38 which is positioned below the pump drive compartment 37 and pc board compartments 39 and 41 which are mounted on the other side of the framework 36. The pump drive compartment 37 is provided with a support plate 46 which forms a part of the framework 36. A stepping motor 47 is mounted on the support plate 46 and is provided with an output shaft 48 that extends through the support plate 46. Another support plate 56 is provided which is mounted upon posts 57 carried by the support plate 46. A rack 61 is mounted for vertical reciprocation in a bracket or slide 62 which is mounted upon the support plate 56. A pinion 63 engages the rack 61 and is mounted upon a shaft 64 that is carried by a coupling 66 mounted upon the output shaft 48.

Yieldable spring means reduces the drive system compliance by preloading rack 61 in tension and consists of a spring 71 which has one end connected to a pin 72 which travels with the rack 61 and which has the other end. connected to a pin 73 which is mounted upon the support plate 56. Motor position switch means 75 is provided for giving a timing signal when the rack 61 has reached its lowermost position and consists of infrared sensing means in the form of a light emitting diode 76 and a photosensor 77 carried by a bracket 78 mounted on the plate 46. A vane 79 mounted on the coupling 66 is adapted to pass between the diode 76 and the photosensor 77 to provide the timing signal.

A disposable pump cassette 81 adapted to be utilized with the pump console 12 is shown in FIGS. 4 and 5 and consists of a pump body 82 which is provided with two portions 82a and 82b in which portion 82a is dome-shaped and forms a pump chamber 83 and portion 82b is semi-cylindrical and forms a bubble chamber 84. A pump base 86 is secured to the lower extremity of the pump body 82 by suitable means such as ultrasonic welding. The pump base 86 is provided with a cylindrical depending open ended portion 87 which opens into the chamber 83. A piston 88 is mounted for reciprocatory movement within the cylindrical portion 87 and extends upwardly into the chamber 83. A boot 89 of a suitable material such as a silicon rubber is positioned over the piston 88 and has its lower outer margin secured between the pump base 86 and a boot retainer 91.

An O-ring 92 is disposed below the boot 89 and is in sealing engagement with the cylindrical surface of the piston 88 as shown particularly in FIG. 5. A seal member 93 of a suitable material such as silicone rubber is disposed in the pump chamber 83 and has its outer margin clamped between the pump body 82 and a retainer 94. An offset flapper valve member 95 as shown is provided with a tapered construction so that its thickness decreases progressively towards the inner margin of the same. The valve member 95 overlies a flow passage 96 which is in communication with a flow passage 97 that extends into a semi-annular flow passage 98 opening into the bubble chamber 84.

The boot retainer 91 is provided with a cylindrical upstanding portion 101 which opens into the interior of the bubble chamber 84. The cylindrical portion 101 is provided with a flow passage 102 which extends downwardly through the same and through the pump base 86 to inlet connection 104. A resealable membrane cap 106 formed of a suitable material such as rubber is mounted on top of the portion 82b of the pump body 82 and encloses the chamber 84. A plunger or lower piston rod 108 is provided which is secured to the piston 88 and depends downwardly therefrom. The piston rod 108 is provided with a head 109 which is adapted to seat within a recess 111 provided in the upper extremity of the rack 61. A retaining cap 112 having an opening 113 through which the piston rod 108 extends is secured to the lower extremity of the cylindrical portion 87. A protrusion 114 is provided on the upper extremity of the pump body 82 and is provided with a flow passage 115 therein which opens into the pump chamber 83.

In order that the pump cassette be disposable, it is desirable that the pump cassette be formed of inexpensive materials. With the exception of the boot 89, the seal and valve member 93, the o-ring 92 and the cap 106, all of the remaining parts can be formed of a suitable material, such as plastic. The use of clear plastic makes it possible to see into the pump chamber 83 and into the bubble chamber 84.

The protrusion or outlet 114 is sized so that a tubing 116 can be bonded to it. The tubing 116 is provided with a fitting 117 and is adapted to be connected to an auto-inflatable retroperfusion balloon catheter 118 of a conventional type which is introduced into the venous side of the heart during retroperfusion operations as hereinafter described The catheter 118 is provided with an inflatable balloon 119. The tubing 123 is adapted to be connected to an arterial blood supply as hereinafter described.

The pump console 12 is provided with a top wall 126 which forms a part of the framework 36. It is also provided with a bottom wall 127, a rear wall 128, side walls 129 and 131 and a front wall 132. The front wall 132 is provided with an upper vertical portion 32a and lower inclined portion 132b. The compartment 124 opens to the exterior through a slot 133 in the side wall 129. The top wall 126 is provided with an opening 136 through which the lower extremity of the disposable pump cassette 81 can extend and in particular so that the retaining cap 112 can engage lips 137 which extend into the opening 136 at the time that the head 109 is slid into the recess 111. Yieldable means is provided for retaining the disposable pump cassette 81 in a predetermined position on the top wall 126 and includes a pair of spring urged detents 138 which are carried by the top wall 126 adjacent the opening 136 and which are adapted to engage dimples 139 provided on the bottom side of the pump base 86.

The top wall 126 is provided with another slot 141 which is adapted to receive the protrusion 104 and the tubing 123 carried thereby. As the pump cassette 81 is moved into place, the portion 82b of the pump body 82 forming the bubble chamber 84 is moved in between a pair of spaced apart members 143 which are mounted on a post 144 provided on the top plate or wall 126.

Infrared sensing means 145 is provided for sensing the level of liquid in the bubble chamber 84 and consists of a pair of light emitting diodes 146 and photodiodes 147 which are carried by the members 143. One light emitting diode 146 is provided on each of the members 143 and one photodiode 147 is provided on each of the members with the photodiodes facing the light emitting diodes. The photodiodes are provided to sense when the level of the blood within the chamber 84 drops below a predetermined level to stop the pumping action as hereinafter described.

A pinch off valve mechanism 151 for cutting off arterial blood flow through the tubing 123 is provided on the side wall 129 of the pump console 12 and consists of a bracket 152 which is secured to the side wall 129. An electrical solenoid 153 is mounted on the bracket and is adapted to operate a clamping jaw mechanism 154 provided on the bracket 152. The clamping jaw mechanism 154 is of a conventional type and is spring loaded into an open position and is provided with a slot 156 therebetween through which the tube 123 can extend. When the solenoid 153 is energized, the slot 156 is closed to pinch off flow through the compliant tubing 123. As soon as the solenoid 153 is de-energized, arterial blood flow resumes through the tubing 123.

Figure 2:
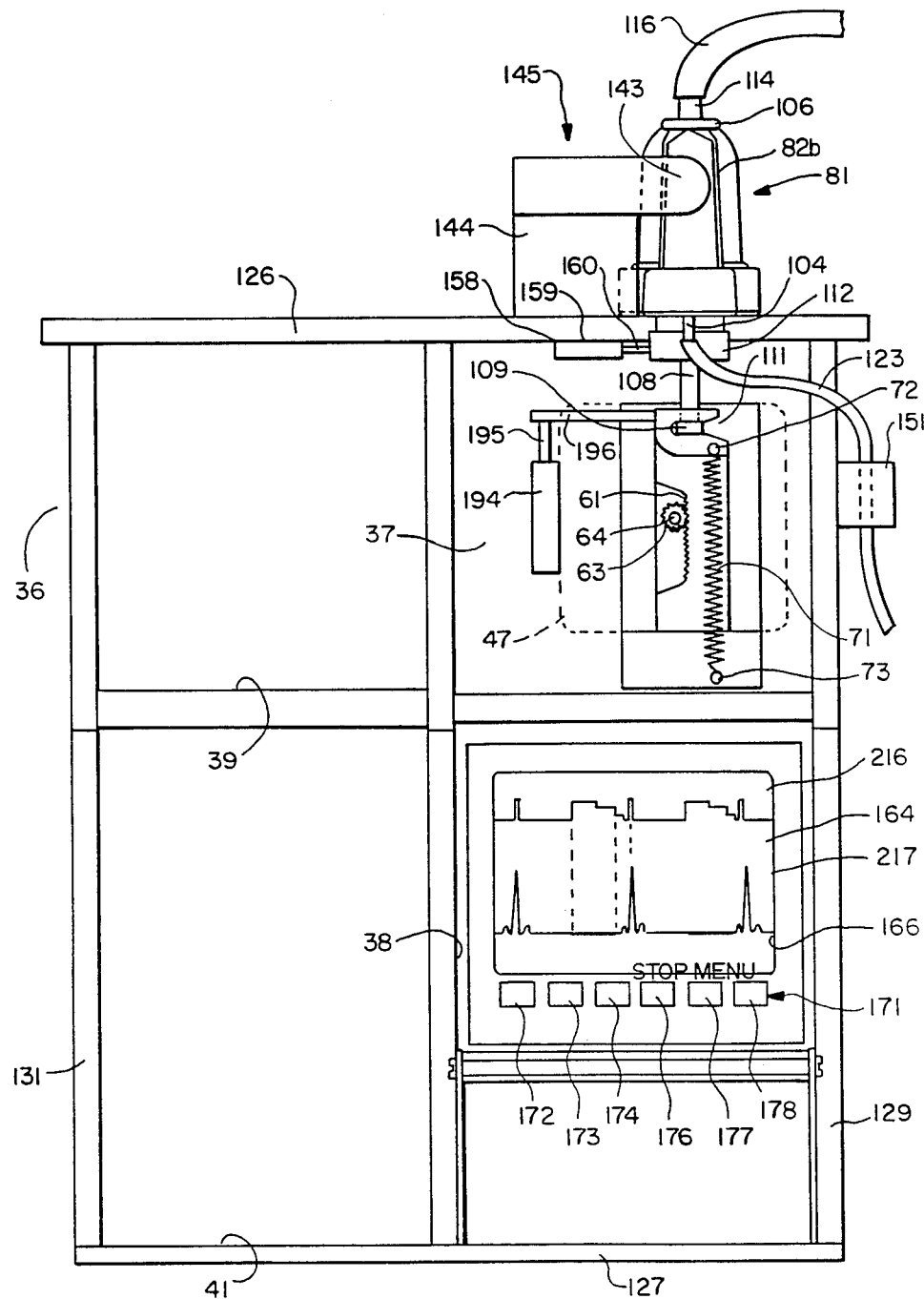
FIG. 2 is a front elevational view of the controller shown in FIG. 1.
Figure 3:
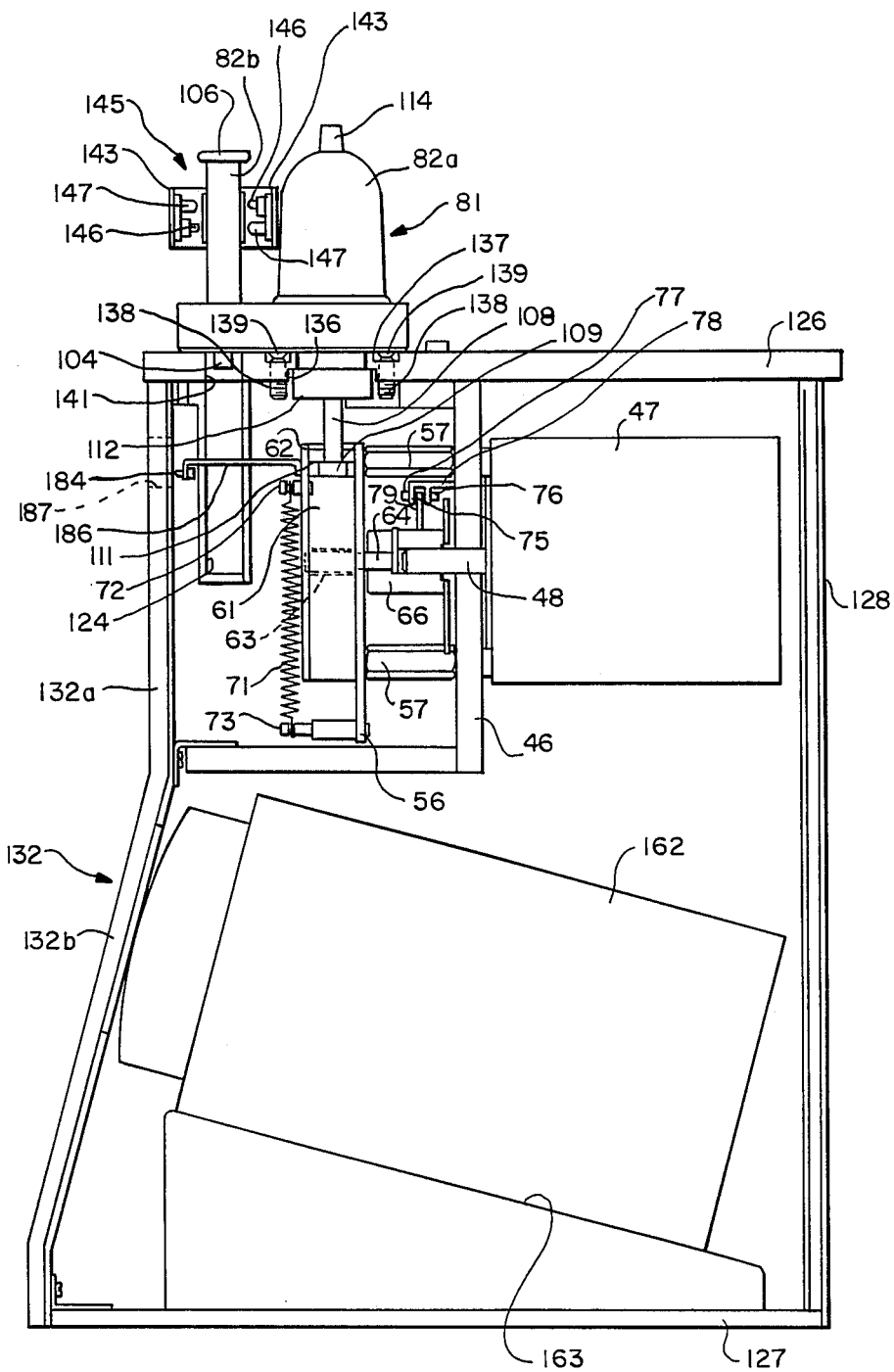
FIG. 3 is a side elevational view of the apparatus shown in FIG. 1.

Cassette position sensing means 158 is provided for ascertaining when the pump cassette 81 is properly positioned on the pump console 12. This sensing means 158 consists of a microswitch 159 mounted on the top plate 126 (see FIG. 2). It is provided with an operating arm 160 which engages the retaining cap 112 of the cassette 81.

A cathode ray tube 162 is mounted in the monitoring compartment 38 and is seated upon an inclined plane 63 mounted within the framework 36. The cathode ray tube 162 is provided with a screen 164 which is visible through an opening 166 provided in the front panel 132. A keyboard 171 is provided below the screen 164 and is provided with 6 push buttons 172, 73, 174, 176, 177 and 178.

Push button 172 is a spare. Push button 173 which carries an up-arrow function and push button 174 which carries a down-arrow function are utilized for increasing and decreasing the number of the various numerical parameters which are utilized for controlling operation of the pump cassette 81 as hereinafter described. The fourth key 176 is a start/stop key and controls the starting and stopping of the pump. The key 177 is the menu key and can be utilized for toggling between the ECG display screen and the numeric menu screen. The sixth key 178 is the line key. In addition to the main CRT screen 164 that can be viewed from the front panel 132 two three digit light emitting diode displays 181 and 182 are provided. Display 182 is for the flow rate setting for the apparatus and display 181 is for displaying the heart rate which is being sensed from the electrocardiogram.

Another display on the front panel shows the travel of the rack 61 and is comprised of a light emitting diode 184 supported on a bracket 186 mounted on the rack 61 so that it travels vertically with the rack. The travel of the light emitting diode 184 is visible through a slot 187 provided in the front panel 132.

Three connectors 191, 192 and 193 are provided in the lower left-hand side of the front panel 132. The connector 191 is used for receiving the electrocardiogram signal output which typically is a one volt peak-to-peak signal coming from an external ECG monitor. The connector 192 is utilized for providing the pump stroke signal which can be utilized in a strip chart recorder for externally recording the operation of the apparatus. The third connector 193 provides a piston position signal which can be utilized in a strip chart recorder for externally recording piston 108 position. This piston position signal is supplied by a linear potentiometer 194 having a movable armature 195 connected to plunger 108 by an arm 196. Alternatively, the third connector 193 can be utilized as an input for measuring pressure, for example, pressures in the coronary sinus. Conducting cords or cables 197, 199 and 198 (see FIG. 1) are connected to the connectors 191, 192 and 193 respectively.

Figure 6:
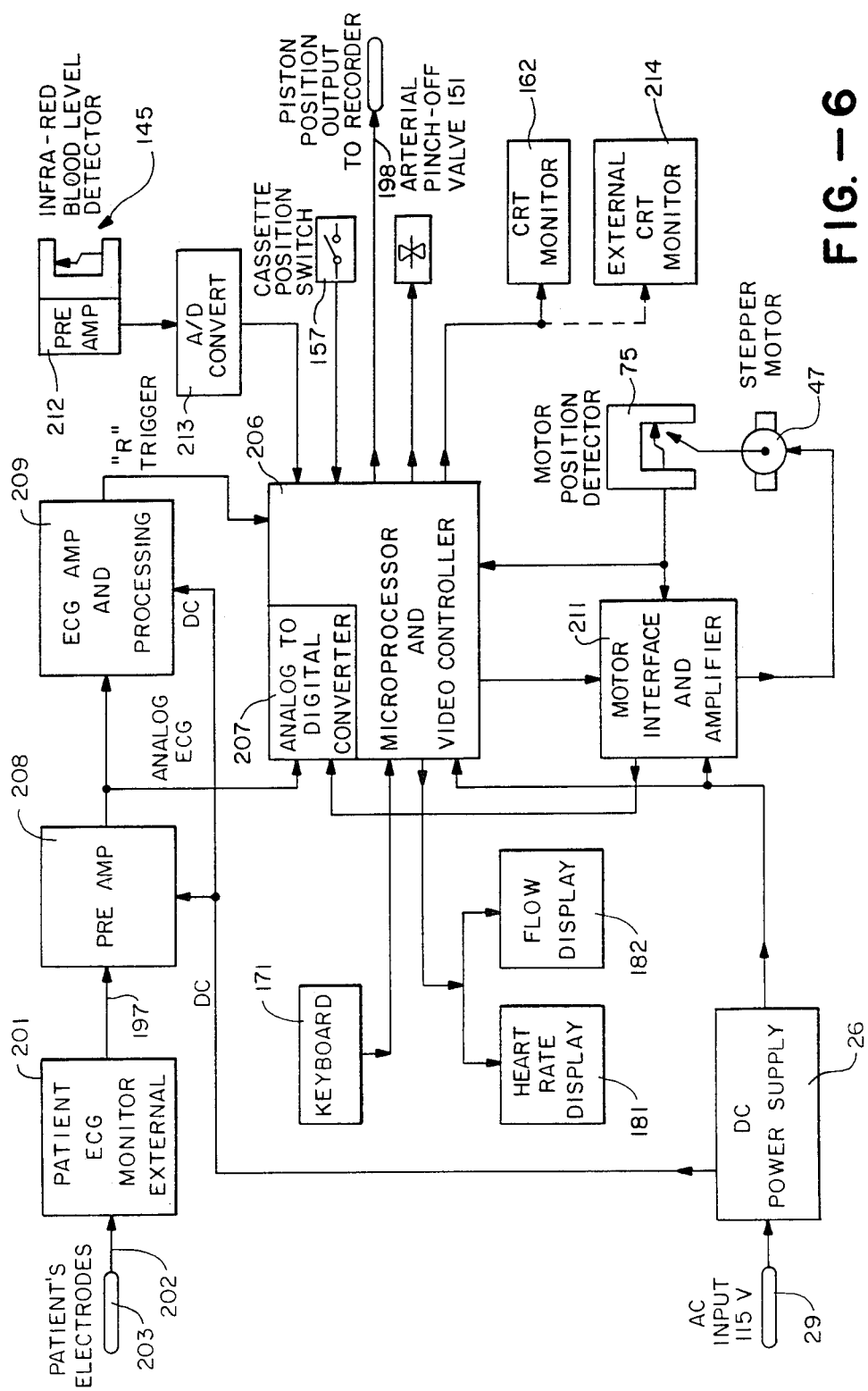
FIG. 6 is a block diagram of the electronics used on the system incorporating the present invention.

As shown in the block diagram in FIG. 6 showing the electronics for the apparatus and system of the present invention, the cord or cable 197 is connected to an external patient ECG monitor 201. The patient ECG monitor 201 is of a conventional type and is provided with conventional leads 202 which are connected to electrodes 203 that are secured to the patient's body in appropriate locations in a conventional manner.

The pump console 12 contains numerous printed circuit boards which contain the circuitry which is shown in FIG. 6. Thus there is provided a microprocessor and video controller board 206 which incorporates an analog-to-digital converter 207. The output from the patient ECG monitor 201 is supplied through a pre amp 208 which supplies its output to the analog-to-digital convertor 207 and also to an ECG amplifier and processing circuitry 209. The circuitry 209 provides an "R" trigger signal to the microprocessor video controller 206. The DC power supply 26 is connected to various components of the circuitry as shown in FIG. 6 as well as to the microprocessor and video controller 206. A motor interface and amplifier board 211 is provided which is used for controlling the stepper motor 47. Various other components of the pump console 12 are interconnected to the microprocessor video controller 206 as shown. These components include the keyboard 171 as well as the heart rate display 181 and the flow display 182. The motor position detector or switch means 75 associated with the stepper motor 47 is connected to the microprocessor and video controller 206 as well as to the motor interface and amplifier board 211. The infrared blood level detector 145 is connected through a preamplifier circuit 212 through an A/D converter circuit 213 to the microprocessor 206. The cassette position sensing switch 158, the arterial pinch off valve assembly 151 and the CRT monitor 162 are also connected to the microprocessor and video controller 206. The microprocessor 206 supplies an output to the connector 192 which can be connected to a strip chart recorder. If desired, as shown in FIG. 6, an additional external CRT monitor 214 can be utilized.

Operation and use of the retroperfusion apparatus and system in performing the method of the present invention may now be briefly described as follows. Let it be assumed that a patient has been identified in which it is desired to utilize a retroperfusion procedure. The equipment dolly or stand 14 is brought to the patient or conversely, the patient is brought to the equipment dolly where it is located. The cord 28 or 31 is connected into an appropriate power outlet in the hospital. The operator then observes the position of the rack 61 by noting the location of the small light emitting diode 184 which is viewable through the slot 187 provided on the front panel 132. This diode 184 should be at the bottom or home position. If it is not in the home position, the plunger 108 should be shifted in the cassette 81 so that it is in an appropriate position so that it can be inserted into the pump console 12. The pump cassette 81 can then be positioned so that the retaining cap 112 enters the opening 136 so that the head 109 carried by the piston plunger 108 can enter the slot or recess 111 provided at the top of the rack 61. At the same time this is occurring, the bubble chamber 84 is introduced into the infrared level detector 145. The on/off switch (not shown) for the power supply 26 can be operated to supply power to the control pump console 12. The screen 164 of the CRT monitor 162 should then be viewed to see whether or not the top trace 216 on the screen is a straight line. This trace 216 represents the pump stroke when the pump is being operated.

The cable 197 is then connected to the patient ECG monitor 201 and the ECG electrodes 203 are attached to the patient. The R wave signal on the video monitor 162 is then observed by observing the lower trace 217 on the screen 164 of the video monitor. The rate of rise of the R wave should always be greater than that of the T wave. Appropriate selection of ECG leads can be made on the patient to adjust the quality of the ECG signal. The cable 199 can then be connected to the strip chart recorder for recording the pump stroke cycle trace.

With an empty pump cassette in place, the start button 176 on the keyboard 171 can be pressed which will cause operation of the stepper motor 47 to cause operation of the rack 61 to operate the plunger 108 of the cassette. Unless preamp 212 of the blood level sensor 145 senses an appropriate blood level, only one pump stroke is taken and the pump stops, indicating an alarm condition.

The pump console 12 may now be set to the desired parameters. For example, an initial flow rate of 100 milliliters per minute per EKG can be set by pressing the menu button 177 to cause the menu screen to be displayed. The up and down keys 173 and 174 can then be utilized to select the correct value for flow. As soon as these values have been set the menu button 177 can be again pressed to enter the new value and execute the flow adjustment. The screen will again display the ECG signal and the pump stroke trace.

Utilizing conventional aseptic techniques, a conventional supply catheter 221 can be placed in the femoral artery 222 of the patient and connected to the tubing 123 to obtain a supply of arterial blood. The inflatable retroperfusion balloon catheter 118 is placed in the great cardiac vein 226 approximately 2 to 3 centimeters proximal to the anterior interventricular vein via the coronary sinus. Proper placement of the catheter 118 is confirmed under fluoroscopy by observing the free flow of a radiopaque solution around the catheter in the atrium during systole. A disposable pressure transducer (not shown) can be secured to the proximal end of the retroperfusion catheter's pressure lumen if it is so equipped, and can be connected to the cabling 198 which is connected to the pressure connector 193 provided on the front panel 132.

A sterile pump cassette 81 is placed on the pump console 12. The apparatus is then primed with a sterile heparinized saline solution. Any air bubbles which appear in the apparatus are removed by using a syringe to penetrate the cap 106 and withdrawing air from the bubble chamber 84. In order to ensure that all air is withdrawn from the apparatus, a syringe can also be utilized to draw blood back through the outlet tubing 116 and retroperfusion catheter into the injection site 117a to ensure that all air has been removed.

As soon as this has been accomplished, the pump can be placed in operation. As arterial blood is delivered through the coronary sinus catheter during diastole, the blood automatically inflates the balloon at the end of the auto-inflatable retroperfusion balloon catheter 118. This retards the efflux of blood from the regional coronary veins and permits effective retrograde delivery of arterial blood to the myocardium of the heart. Termination of the retrograde catheter perfusion at end of diastole, automatically deflates the balloon and permits antegrade coronary sinus drainage of venous blood from the myocardium into the right atrium during systole.

More specifically, the operation of the apparatus and in particular, the circuitry which is shown in FIG. 6 may now be described. The one volt peak-to-peak signal which is supplied from the external ECG monitor 201 has been prefiltered to approximately 150 hertz high frequency rolloff. A signal is supplied to the preamplifier 208 which accomplishes additional filtering and also supplies a signal to the A/D converter 207 connected to the microprocessor 206. A signal is also supplied from the preamp 208 to the ECG amplifier and processing circuitry 209 which is utilized to ascertain location of the R wave peak. This is accomplished by taking the electronic derivative of the signal to find the maximum slope in the wave form. This information is supplied as a signal on the R trigger circuit to the microprocessor 206. The microprocessor 206 has the capability of correlating the pattern which is generated by the A/D converter 207 based upon the ECG monitor and compares it with an independently generated R trigger circuit signal being supplied by the ECG amplifier and processing circuitry 209 to ascertain whether or not there is an agreement that an R wave has been detected which can be utilized for triggering the operation of the stepper motor 47.

The output of the microprocessor video controller 206 feeds signals to the stepper motor 47 that are phased in relationship to the stepper motor to create approximately 500 steps per inch of operation of the motor in forward and then in reverse and causing a resultant travel of the piston 88 in the pump cassette 81 between the upper and lower limits of movement for the piston 88. These steps of the stepper motor, and the rate at which these steps are taken are controlled by the microprocessor 206 utilizing a lookup table and are based upon the heart rate input that is sensed by the ECG monitor 201 and the delivery setting which has been inserted by the physician into the pump console 12 by operation of the menu key 177 and the up and down keys 173 and 174 as hereinbefore described. In this manner, the microprocessor 206 determines precisely the upstroke time and speed as well as the pause time and the downstroke time and speed. The microprocessor 206 is capable of assimilating arrhythmias and abnormal ECG events. Typically the microprocessor 206 initiates the pump cycle at approximately 45% and terminates at 95% of the R to R period if the heartbeat is steady. The desired steadiness can be defined, e.g., no more than 10% change during the past eight heartbeats. If the rate is changing more rapidly, the pump is started later depending upon the rate of change to avoid premature pumping and straining of the heart. The pump cycle is always terminated at the beginning of a new R wave. After a very irregular beat the pump skips a pump cycle until the heartbeat stabilizes, all under the control of an algorithm.

As hereinbefore explained there are three feedbacks to the microprocessor from the stepper motor 47, from the pump cassette 81, and from the infra-red blood level detector 145. The first is the bottom of stroke indication from the motor position detector 75. The second input to the microprocessor 206 is the cassette position switch 158 which informs the microprocessor whether or not the cassette is actually connected to the stepper motor rack 61. Thus, if the cassette is improperly placed, the microprocessor 206 will stop the pumping operation. Information is also supplied from the infrared blood level detector 145 to the microprocessor 206 and causes the microprocessor 206 to shut down the pumping action when air bubbles are sensed in the blood or when the blood level within the bubble chamber 84 falls below the level of either of the infrared sensors of the blood level detectors 145.

The microprocessor 206 has been programmed so that the pump stroke will start at 45% of the R to R interval (the R period) and terminates at approximately 95% of the R to R interval. In programming this pumping operation, it has been found it is desirable to program the microprocessor 206 so that signals to the stepper motor 47 are entered twice as fast on the upstroke so as to leave approximately one half of the time allotted for the upstroke for L pause time after which the downstroke is commenced. The downstroke is accelerated in order to cause better deflation of the auto inflatable balloon 119 at the and of the catheter 118 and also to more quickly reduce the pressure from the coronary sinus caused by the pump stroke.

Such a flow pattern is shown in the traces shown in FIG. 7. The traces show that pumping into the coronary sinus actually begins at the end of systole or in other words at the end of the arterial pressure wave. Utilizing a pause between the upstroke and downstroke, the slope of the rise of flow is much steeper and achieves peak flow much earlier in the R to R cycle which makes it possible to achieve peak pressure in the coronary sinus earlier in the R to R cycle. This helps to prevent or avoid the generation of overpressures or collisions between the pressure due to flow caused by the pump and the pressure wave due to arterial pressure of the next systole. Thus it can be seen that this helps to avoid possible hemorrhaging in the heart. A downward or receiving portion of the flow occurs prior to the occurrence of the next R wave, thus pressure is removed more rapidly from the coronary sinus.

With such use of a pause phase, the same amount of blood can be delivered between the R to R peak but is delivered more rapidly and more appropriately in the diastolic time window. In addition the pressure is removed more rapidly to prevent any possible collision from the systolic arterial pressure wave. By adding the pause at the end of the upstroke, the pressure generated completely depletes and translates into maximum blood flow. The downstroke does not occur until after this pressure has been completely dissipated through the catheter and maximum flow has been expelled through the catheter. As the downstroke occurs, a greater negative pressure is created than would be the case without a pause. This greater negative pressure facilitates collapse of the balloon 119 of the auto-inflatable balloon catheter 118.

Thus it can be seen there are two effects from such a procedure. One is to deliver the pressure wave and the flow earlier in the R to R cycle and the other is to allow greater flow through the catheter by allowing the buildup of pressure to deplete itself and translate into greater blood flow with a subsequent improved collapse of the balloon.

In FIGS. 7A, 7B, 7C and 7D, there are shown four strip chart recordings which show the response of the pump 81 in response to heart rate variation. In achieving the data which is shown in FIGS. 7A, 7B, 7C and 7D, a retroperfusion apparatus and system of the present invention was utilized with the pinch valve assembly 151 being utilized for controlling the arterial blood flow. A patient ECG simulator was utilized to provide a normal rhythm. A conventional flow meter and a strip chart recorder were utilized. A saline solution was placed in a bag at 6 feet in elevation to simulate arterial pressure. A 7 French catheter with a 5 millimeter balloon was utilized. The catheter tip was introduced into a graduated cylinder so that the amount of saline solution which was pumped could be measured. In carrying out the tests, a calibration was performed for 0 to 100 milliliters per minute flow to calibrate the strip chart versus the graduated cylinder. In each of the flow settings of 20 to 120 milliliters per minute at 20 milliliter increments, the delivered mean flow was recorded on the strip chart recorder at heart rate settings of 60, 80, 100, 120 and 150 beats per minute. Recordings were made at both slow and fast recording speeds with each setting as shown in FIGS. 7A, 7B, 7C and 7D. After the calibration had been completed, the flow was set at 80 milliliters per minute and the heart rate was varied through 40, 60, 80, 100, 120 and 150 beats per minute at a fast strip chart speed and then varied through 150, 120, 100, 80, 60 and 40 beats per minute at slow speed for compressed recording. The results of the tests are shown in the traces in 7A, 7B, 7C and 7D.

The trace 231 is FIG. 7A, shows the electrocardiogram with the R peaks 232 as they are changed from a rate of 150 beats per minute to 120, 100, 80, 60, and 40 beats per minute. The phasic timing of the pump stroke is shown by the trace 236 in FIG. 7B. The highest level 237 of the trace indicates the upstroke time. The next lower level 238 indicates the duration of time that is occupied by the pause state where the pump piston is at its highest position and is held there for a predetermined period of time. The next level 239 indicates the time taken for the downstroke. The lowest level 241 indicates the pause or waiting time before the next trigger signal arrives to start the upstroke.

The trace 246 which is shown in FIG. 7C shows the actual pump piston position with respect to time. The movement of the piston during the upstroke is indicated by the upwardly sloped portion 246a of the trace 246. The pause for the piston at the upper limit of its travel is indicated by the flat portion 246b and the downwardly inclined slope portion 246c indicates the downward stroke of the piston. The flat portion 246d represents the pause before the next upstroke of the piston is started.

The trace 251 which is shown in FIG. 7D shows the time-averaged mean flow output from the pump through a calibrated flow meter and shows that a substantially constant output flow as, for example, 80 milliliters per minute for which the pump console 12 was set is achieved even though the beats per minute change radically. The trace in FIG. 7C show how this was accomplished. As the beats per minute decreases, as for example, 150 for the initial pump stroke as shown by the level portion 246b, which is represented by the level 247 for 150 beats per minute. As the heart rate decreases, a larger volume of blood must be pumped with each stroke and therefore the stroke length is increased as represented by level 248 for 120 beats per minute, level 249 for 100 beats per minute, level 251 for 80 beats per minute, level 252 for 60 beats per minute and level 253 for 40 beats per minute. The trace 256 in FIG. 7D shows that the output of the pump remains substantially constant through the entire operating range from 150 to 40 beats per minute. Thus it can be seen that the microprocessor 206 senses the change of rate of the heart beats and adjusts the upstroke time, the upstroke speed, the pause time and the downstroke time so that with the reduced number of strokes per minute increased volume is produced by the pump each time a stroke is made so that the resultant mean flow from the retroperfusion apparatus is substantially constant.

It has been found that once the system has been primed, there is no accumulation of air within the system because the system is sealed.

From the foregoing, it can be seen that there has been provided a retroperfusion apparatus system and method which has many advantages. The microprocessor controlled stepper motor drive provides a positive control over the pump stroke and provides a powered upstroke and a powered downstroke by forward and reverse motion of the stepper motor. The precisely controlled powered downstroke contributes to the balloon deflation. The microprocessor control which is utilized makes it possible to precisely detect the R waves by ascertaining the maximum positive slope within the ECG waveform and supplies a signal which is correlated with software in the microprocessor to ascertain whether in fact an R peak has occurred to therefore make possible a more positive and precise identification of the R wave. A direct coupling is provided between the stepper motor and the piston of the pump which direct coupling is obtained by the use of a rack and pinion.

Numerous safety features have been provided in the apparatus and system. In addition, the pinch-off valve in the arterial line clamps off the arterial line when the system is stopped or a fault alarm or condition occurs. This prevents flow through of the arterial blood. Thus, it can be seen that the pinch-off valve prevents passive flow through of arterial blood under arterial pressure through the system from the arterial side to the venous side. If the pinch-off valve were not present, it would be possible for such passive arterial blood flow to be as much as 30 milliliters per minute which could eventually fill the auto inflatable balloon and occlude the sinus for egress of blood which could have very deleterious effects on the patient.

What is claimed is:

1. In a control apparatus for supplying arterial blood of a patient to the venous side of the patient's heart, a pump having an inlet adapted to be coupled to an artery of the patient and an outlet, a catheter coupled to the outlet and adapted to be connected to a vein of the patient, the catheter having an inflatable balloon mounted thereon, movable means forming a part of the pump movable through a pump stroke for moving a liquid from the inlet to the outlet of the pump, a stepper motor, means coupling the stepper motor to the movable means, and electronic circuitry for driving the stepper motor, the electronic circuitry including means for sensing the presence of an R wave in an electrocardiogram of a patient and for operating the stepper motor in response to the sensed R wave.

2. Apparatus as in claim 1 wherein the pump is in the form of a removable disposable pump cassette.

3. Apparatus as in claim 2 wherein the movable means is a piston mounted for reciprocatory movement in the pump cassette in upstroke and downstroke directions and wherein the stepper motor is rotated in one direction during the upstroke direction and wherein the stepper motor is operated in a reverse direction during the downstroke direction.

4. Apparatus as in claim 1 wherein said electronic circuitry includes a microprocessor for generating digital output signals for operating the stepper motor.

5. Apparatus as in claim 4 together with a bubble chamber coupled to the pump for receiving arterial blood and wherein said electronic circuitry includes detecting means associated with the bubble chamber and connected to the microprocessor for informing the microprocessor when bubbles of air appear in the arterial blood supply and also when the amount of arterial blood drops below a predetermined level to stop operation of the pump.

6. Apparatus as in claim 4 together with a pump console, wherein the stepper motor is mounted in the pump console and wherein the means coupling the stepper motor in the movable means is also in the pump console and electrical means carried by the pump console and adapted to be engaged by the pump for ascertaining when the pump is in a proper position and for supplying an electrical signal to the microprocessor when the pump is improperly positioned in the pump console to cause the microprocessor to initiate an alarm condition.

7. Apparatus as in claim 4 together with means coupled to the microprocessor for cutting off arterial blood flow through the pump when movement of the movable means ceases.

8. Apparatus as in claim 7 wherein said means for cutting off arterial blood flow includes a pinch-off valve mounted on the pump console for controlling the flow of arterial blood through the pump and means connecting the pinch-off valve to the microprocessor for controlling operation of the pinch-off valve.

9. Apparatus as in claim 4 together with means for sensing the position of the stepper motor connected to the microprocessor for supplying information to the microprocessor as to the location of the movable means of the pump.

10. Apparatus as in claim 4 wherein the microprocessor is programmable and has been programmed to start the pump stroke at approximately 45% of the R wave to R wave interval and terminates at approximately 95% of the R wave to R wave interval and wherein the digital output signals to the stepper motor for the upstroke are supplied during an initial portion of the time period for the upstroke so that a pause is provided at the upper extremity of the pump stroke and prior to the downstroke so as to permit any pressure buildup in the pump to dissipate and to permit a continued flow of blood to occur prior to the downstroke.

11. Apparatus as in claim 10 wherein the microprocessor has been programmed so that approximately one half of the time allotted for the upstroke is allotted for the pause after the upstroke.

12. Apparatus as in claim 4 wherein said electronic circuitry includes means to cause a predetermined mean flow to be supplied to the patient which is independent of the heart rate of the patient.

13. Apparatus as in claim 12 wherein said means to cause a predetermined mean flow includes a program in the microprocessor.

14. Apparatus as in claim 4 together with an external ECG monitor adapted to be coupled to the patient and supplying an R trigger circuit signal and wherein the microprocessor includes means for creating a pattern from the R trigger circuit signal and means for comparing the signal received from the external ECG monitor with the pattern for ascertaining whether the R trigger circuit signal received is appropriate for operating the pump.

15. Apparatus as in claim 4 together with display means coupled to the microprocessor for displaying an electrocardiogram, the R wave and the pump stroke in a timed relationship.

16. Apparatus as in claim 4 wherein said electronic circuitry includes detecting means connected to the microprocessor for informing the microprocessor of the arterial pressure of the patient.

17. Apparatus as in claim 16 wherein said detecting means for detecting arterial pressure is used to detect the presence of diastole in a patient independently from the electrocardiogram R wave signal.

18. Apparatus as in claim 4 wherein said electronic circuitry includes detecting means connected to the microprocessor for supplying coronary sinus pressure of the patient to the microprocessor.

19. A method for supplying arterial blood into a venous region of the heart, comprising taking an electrocardiogram of the patient, ascertaining when an R wave is present in the electrocardiogram, supplying arterial blood from the patient under positive pressure into a venous region of the heart for a predetermined period of time in accordance with the R wave of the patient, providing a pause period for a predetermined period of time to permit any positive pressure created to be dissipated and to permit continued flow to occur and thereafter allowing antegrade flow of venous blood from the heart for a predetermined period of time in accordance with the R wave of the patient.

20. A method as in claim 19 wherein the pause period is made substantially equal to the period during which arterial blood is being introduced under positive pressure.

21. A method as in claim 20 wherein the time for antegrade flow of arterial blood is made to be substantially equal to the period of time in which arterial blood is supplied retrograde under positive pressure and the period during which the pause occurs.

22. A method as in claim 19 together with the steps of sensing any change in heart rate and making adjustments in the arterial blood supplied so that arterial blood is supplied to the patient at a substantially constant mean blood flow rate.

23. A method as in claim 19 together with the step of independently generating an R-wave pattern, comparing the R wave from the electrocardiogram with an independently generated R wave pattern to ascertain whether on R wave has been received from the patient which is appropriate for supplying arterial blood into a venous region of the heart.

24. A method as in claim 19 together with the step of detecting bubbles of air in the arterial blood supply, cutting off the arterial blood flow, and initiating an alarm.

25. A method as in claim 19 together with the step of collecting arterial blood in a reservoir, detecting when the level of arterial blood in the reservoir drops below a predetermined level and initiating an alarm.

26. A method as in claim 19 to initiate an alarm if the heart rate exceeds a predetermined value.

27. A method as in claim 19 to initiate an alarm if the heart rate drops below a predetermined value.

28. A method as in claim 19 for use with a pump having a movable means for pumping arterial blood together with the step of sensing the location of the movable means in the pump to initiate an alarm if the location of the movable means does not change in a predetermined manner.

29. A method as in claim 28 together with the step of determining whether an R wave of the patient is appropriate for operation of the movable means, and whether aborting continued movement of the movable means during the R wave of the patient is deemed to be inappropriate for operation of the movable means.

* * * * *